and pharmaceutical chemists. Berlin: Walter de Gruyter.1997, p. 246 (3 pages in total).*

(12) United States Patent
Tambi

(10) Patent No.: US 8,916,614 B2
(45) Date of Patent: Dec. 23, 2014

(54) LINDANE LOTION AND METHODS

(75) Inventor: Brian Tambi, Lake Forest, IL (US)

(73) Assignee: Wockhardt EU Operations (Swiss) AG, Zug (CH)

(*) Notice: Subject to any disclaimer, the term of this patent is extended or adjusted under 35 U.S.C. 154(b) by 1454 days.

(21) Appl. No.: 12/032,471

(22) Filed: Feb. 15, 2008
(Under 37 CFR 1.47)

(65) Prior Publication Data
US 2009/0105276 A1     Apr. 23, 2009

Related U.S. Application Data

(60) Provisional application No. 60/890,667, filed on Feb. 20, 2007.

(51) Int. Cl.
| | | |
|---|---|---|
| *A61K 31/4965* | (2006.01) |
| *A61K 31/025* | (2006.01) |
| *A61K 31/44* | (2006.01) |
| *A61K 31/4402* | (2006.01) |

(52) U.S. Cl.
CPC ............ *A61K 31/025* (2013.01); *A61K 31/4402* (2013.01)
USPC .................. 514/747; 514/255.04; 514/357

(58) Field of Classification Search
USPC ..................... 514/255.04, 747, 357
See application file for complete search history.

(56) References Cited

U.S. PATENT DOCUMENTS

| | | | | |
|---|---|---|---|---|
| 4,824,865 | A | * | 4/1989 | Bowser et al. ............... 514/558 |
| 6,998,113 | B1 | * | 2/2006 | Traynor et al. ............... 424/59 |
| 2004/0013700 | A1 | * | 1/2004 | Precopio ..................... 424/405 |
| 2004/0018241 | A1 | * | 1/2004 | Houze et al. ............... 424/486 |
| 2006/0121073 | A1 | * | 6/2006 | Goyal et al. ............... 424/405 |
| 2007/0086974 | A1 | * | 4/2007 | Gawande et al. .......... 424/78.15 |

OTHER PUBLICATIONS

Drug Facts and Comparisons, 1994 edition, Wolters Kluwer Company, pp. 2490-2491.*
Stichele et al., Systematic Review of Clinical Efficacy of Topical Treatments for Head Lice , BMJ: British Medical Journal, vol. 311, No. 7005 (Sep. 2, 1995), pp. 604-608.*
Lange et al., Percutaneous Absorption of Lindane in Healthy Volunteers and Scabies Patients, Arch. Dermatol. Res. (1981) vol. 271 pp. 387-399.*
Ansel et al., Pharmaceutical Dosage Forms and Drug Delivery, 7th edition, Lippincott Williams & Wilkins, 1999, p. 128.*
Rasmussen, The Problem of Lindane, Journal of the American Academy of Dermatology, vol. 5 No. 5 Nov. 1981, pp. 507-516.*
Maunder, Clinical and Laboratory trials employing carbaryl against the human head-louse, *Pediculus humanus capitis* (de Geer), Clinical and Experimental Dermatology (1981) vol. 6(6) pp. 605-612.*
Brandenberger, et al , Analytical toxicology: for clinical, forensic, and pharmaceutical chemists. Berlin: Walter de Gruyter.1997, p. 246 (3 pages in total).*

* cited by examiner

*Primary Examiner* — T. Victor Oh
(74) *Attorney, Agent, or Firm* — Winston & Strawn LLP

(57) ABSTRACT

The present invention is directed to methods of treatment for scabies using different concentrations of lindane lotions for varying contact times. Compositions of low concentration lindane lotions are also included.

12 Claims, 3 Drawing Sheets

Comparison of $T_{max}$ by Treatment Regimen

LINDANE LOTION AND METHODS

This application claims the benefit of provisional application 60/890,667 filed Feb. 20, 2007.

TECHNICAL FIELD

The present invention relates generally to methods of treatment of scabies by topically applying lindane lotion. The invention further relates to compositions of lindane lotion.

BACKGROUND OF THE INVENTION

Scabies Infestation

Scabies is a public health concern of global proportion, affecting an estimated 300 million people worldwide each year [Chosidow, O., *Clinical practices. Scabies*"; N. Engl. J. Med.; Vol. 354, pp. 1718-1727, 2006]. The disease dates back to the 1700's when the *Sarcoptes scabiei* mite was first identified as the culprit pathogen. As a highly contagious infectious disease of the skin, scabies is readily spread by direct physical contact. It affects people of all races and social classes and occurs in all age groups and both genders [Wendell, K. et al., "*Scabies and pediculosis pubis: an update of treatment regimens and general review*"; Clin. Infect. Dis.; Vol. 35; pp. S146-S151, 2002]. It is a common sexually transmitted disease; however, it is often transmitted nonsexually and is easily spread within families and among people living in crowded conditions [Wendell, K. et al., 2002]. Hospitals, nursing homes, and long-term care facilities are likely sites of scabies epidemics [Habif, T. P., "*Scabies*"; Clinical Dermatology, 4$^{th}$ ed., New York: Mosby; pp. 497-505, 2004; Wendell, K. et al., 2002]. Often referred to as the "itch mite," scabies can cause intense, unbearable itching, clinically described as pruritis [McCarthy, J. S., et al., "*Scabies: more than just an irritation*"; Postgrad. Med. J.; Vol. 80, pp. 382-387, 2004; Orion, E., et al., "*Ectoparasitic sexually transmitted diseases: scabies and pediculosis*"; Clin Dermatol.; Vol. 22, No. 6, pp. 513-519, 2004]. Complications include bacterial superinfection, sepsis, glomerulonephritis and progression to Norwegian or crusted scabies—a more severe, life-threatening form of the disease [Walton, S. F., et al., "*Scabies: new future for a neglected disease*", Adv Parasitol., Vol. 57, pp. 309-376, 2004; Chosidow, O., *Scabies and pediculosis*; Lancet, Vol. 355, pp. 819-26, 2000; Habif, T. P., 2004; Wendell, K. et al., 2002; McCarthy, J. S., et al., 2004].

Today, scabies is increasingly found among immunocompromised patients (i.e., those with HIV infection, cancer, diabetes, organ transplant and those receiving immunosuppressive therapies), where mite burdens can rise to thousands or millions and infestation becomes much more diffuse and widespread over the body. This not only increases the risk of secondary bacterial infection, a potentially serious outcome, but also increases the likelihood of transmission to noninfected individuals [Mathisen G., "*Of mites and men: lessons in scabies for the infectious diseases clinician*" (Editorial response); Clin. Infect. Dis., Vol. 27, pp. 646-647, 1998].

The scabies mite (i.e., *Sarcoptes scabiei*) is a small, rounded, 8-legged parasitic insect that is too small to be seen by the naked eye without magnification. Attracted to warmth and odor, the female mite burrows into the skin, lays eggs, and produces toxins that cause a hypersensitivity reaction and the cardinal symptom of pruritis. Larvae, or newly hatched mites, travel to the skin surface, lying in shallow pockets where they mature into adult mites. Within 2 months, an infected individual may have 25 adult female mites living in the superficial layers of their skin. Within 3 to 4 months, as many as 500 mites may be present [Orion, E., et al., 2004]. Symptoms may not be initially noticeable, especially among patients with good hygiene and those who bathe regularly. Within several weeks, however, pruritis often becomes unbearable, keeping sufferers awake all night.

Scabies is almost always transmitted by close personal contact; only rarely is it contracted by way of contaminated clothing, towels or bedding [Johnston, G., et al., "Scabies: diagnosis and treatment"; BMJ; Vol. 331, pp. 619-622, 2005; U.S. Centers for Disease Control and Prevention (CDC). Parasitic Disease Information: Head Lice Fact Sheet. 2005]. Although scabies is not a condition exclusive to low-income families, it is more often associated with crowded living environments and poor hygienic conditions.

The most common site of scabies infestation in older children and adults, include the genitals, buttocks, fingers, wrists, elbows, armpits, knees and ankles [Habif, T. P., 2004]. Younger children and infants show more widespread involvement, including the palms and soles of the feet [Paller, A. S., et al., "*Insect bites and parasitic infestations*"; Hurwitz Clinical Pediatric Dermatology: A Textbook of Skin Disorders of Childhood and Adolescence; London: Elsevier, Ch. 18, p. 479, 2006]. However, scratching can spread scabies to non-infected areas of the body [Habif, T. P., 2004].

Diagnosis and Treatment

Diagnosis of scabies is generally made clinically by observing the skin burrows created by scabies mites, having the appearance of an excoriated papular rash [Flinders, D. C., et al., "Pediculosis and scabies"; Am. Family Physician, 2004]. Nodules, vesicles, pustles and eczema may also be present but are less specific signs of the disease. Lesions are most often symmetrical in distribution, affecting both the left and right sides of the body [Johnston, G., et al. 2005; Orion E, et al. 2004] Scraping of the burrows and subsequent examination under a microscope for mites, their eggs or fecal matter ("scybala") leads to a definitive diagnosis [Rosen, T., et al., "Cutaneous manifestations of sexually transmitted diseases: scabies"; Med. Clin. North Am.; Vol. 82, pp. 1098-1099, 1998]. However, this technique may not always be revealing and is challenging to perform, even for highly-trained healthcare professionals [Karthikeyan, K., "Treatment of scabies: newer perspectives"; Postgrad. Med. J.; Vol 81, pp. 7-11, 2005]. As such, a definitive diagnosis is not always possible and clinicians must often rely exclusively on the physical examination and patient history.

A number of agents have been used for the management of scabies infestation, with varying rates of efficacy and varying labeled restrictions. Topical therapy is considered the mainstay of treatment, although oral medications are sometimes employed. In the U.S., relatively few agents are FDA approved for this indication. Commonly used treatments include topical permethrin 5% cream*, topical lindane (gamma benzene hexachloride) 1% lotion*, topical benzyl benzoate 10% and 25% lotion or emulsion, topical crotamiton 10% cream*, topical precipitated sulphur 3%-6% lotion or 5%, 10% or 40% in petrolatum, topical allethrin 0.6% aerosol, and oral ivermectin (*FDA-approved indication) [Chosidow 0.2006]. The current treatment for scabies using 1% lindane lotion or cream involves application and then rinsing off after eight hours [Chosidow O. 2006].

Lindane and permethrin are the best studied topical therapies, with comparable rates of efficacy noted in the largest comparative trial to date [Chosidow O. 2006; Schultz, M. W., et al., "Comparative study of 5% permethrin cream and 1% lindane lotion for the treatment of scabies"; Arch Dermatol.; Vol. 126, pp. 167-170, 1990]. Permethrin is approved as a first-line treatment. Lindane is indicated second line because of a relatively greater potential for neurologic side effects, although the vast majority of serious events have almost always resulted from product misuse [U.S. Food and Drug Administration (FDA). Lindane Post Marketing Safety Review. 2003]. Crotamiton is also FDA approved as a first-line intervention but is less effective and not often used. In select patients and settings, oral ivermectin has been shown to be efficacious; however, in the U.S., this is an off-label use [Chosidow O. 2006].

In many parts of the world, including the U.S., drug-resistant forms of scabies have been documented, further complicating disease management and containment of scabies outbreaks. Drug resistance has been reported for all of the commonly used agents, including permethrin, crotamiton, ivermectin and lindane. [Johnston G, et al. 2005; McCarthy J S, et al. 2004] The unpredictable nature of resistance and geographical variability necessitates the need for a variety of approved treatment options.

Lindane (gamma-HCH or BHC)

Lindane is an insecticide, also known as gamma-hexachlorocyclohexane (HCH) and benzene hexachloride (BHC). Its empirical formula is $C_6H_6Cl_6$ and it has the following structural formula:

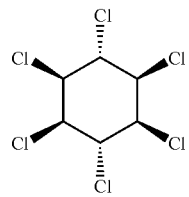 [SMILES: Cl[C@H]1[C@H](Cl)[C@@H](Cl)[C@@H](Cl)[C@H](Cl)[C@H]1Cl]

Lindane exerts its pharmacologic effects via absorption through the chitinous exoskeleton of arthropods (e.g, scabies mite) and subsequent stimulation of the central nervous system (CNS), resulting in convulsion and death.

Lindane Lotion, USP, 1% ("lindane lotion") is approved by the FDA and strictly regulated as a prescription medication for the "second-line" treatment of scabies, meaning it is only indicated after first-line medicines have failed or cannot be tolerated. Lindane lotion has been used successfully in clinical practice for more than 50 years and has proven safe and effective when used as directed. However, systemic drug exposure and the potential risk for neurologic side effects have been raised as a concern. Young children, elderly and individuals of slight stature (weighing less than 50 kg) may be more susceptible to these adverse effects, and cautious use is recommended in these patient types [FDA Public Health Advisory, 2003]. Increased systemic exposure resulting from a higher surface-to-volume ratio has been proposed as a potential underlying factor.

Central nervous system stimulation, with symptoms ranging from dizziness to seizures, has been reported in association with the use of lindane lotion. However, the vast majority of medically significant neurologic events have almost always resulted from accidental oral ingestion or misuse of the product. Indeed, the FDA has quantified serious neurologic side effects associated with the proper use of lindane lotion as rare. [U.S. FDA Postmarketing Safety Review, 2003]. The most common side effects of topical lindane are non-serious reactions of the skin, such as dryness, itching and rash. Nonetheless, lindane medications were relegated to second-line treatment status in 1995 because of concerns relating to product misuse and associated risks. [U.S. Food and Drug Administration (FDA) Public health advisory: Safety of topical lindane products for the treatment of scabies and lice. Mar. 28, 2003]. Lindane medications were also limited to small, single-use 2 oz. bottles (compared with the original 16 oz. multi-dose bottles) in 2003 to further mitigate the risk of improper drug use.

Currently approved guidelines for lindane lotion instruct patients and caregivers to apply a thin film of medicine to the entire body from the neck down and then wash off after 8-12 hours. However, data show that peak blood levels of Lindane are achieved within 4-6 hours following topical application of 1% lindane in a lotion vehicle. [Ginsburg, et al., "*Absorption of Lindane in infants and children*"; J. of Pediatrics; Vol. 91, pp. 998-1000, 1977]. Moreover, inflammatory skin conditions, such as scabies, alter the epidermal barrier, making skin more permeable to topical therapies. [Ginsburg et al., 1977]

The literature reveals few studies of 1% lindane applied for less than 8 hours. For example, an unpublished report by Taplin et al. apparently alleges that there was little difference in the cure rate with application of a 1% lindane lotion for 6 hours, as compared with 24 hours [Shacter, B.; "*Treatment of scabies and pediculosis with lindane preparation. An evaluation*", J. Am. Acad. Dermatol., Vol. 5, pp. 517-527, 1981]. Similarly, a branded 1% lindane solution marketed in France under the tradename Scabecid®, requires only a single 6-12 hour skin application [Buffet, M. et al., "*Current treatment for scabies*," Fundamental & Clinical Pharmacology, Vol. 17 (2003), pp. 217-225].

There are also published reports of the use of lindane at concentrations less than 1% for the treatment of ectoparasitic disease. Specifically, the use of a 0.5% lindane lotion as a topical treatment for head lice has been described; however, the researchers concluded that the formulation was not sufficiently effective against head lice to justify its use for this particular indication. [Stichele, H. et al., "*Systematic review of clinical efficacy of head lice*," British Medical Journal (1995), Vol. 311, pp. 604-608].

In light of these limited and somewhat conflicting reports, there remains a need to further explore methods of enhancing the risk-benefit balance of lindane lotion for the treatment of scabies infestation.

SUMMARY OF THE INVENTION

The present invention relates to a method for the treatment of scabies. The method includes topically applying to a patient's skin in need of treatment a lotion with a concentration of less than 1 percent (w/w) lindane, and leaving the lotion in contact with skin for about 8 hours or less.

The concentration of lindane is generally about 0.2 percent to 0.8 percent (w/w) of the lotion. Preferably, the concentration of lindane is about 0.3 percent (w/w), about 0.5 percent (w/w), or about 0.75 percent (w/w). In another preferred embodiment, the lotion is in contact with the skin for about 90 minutes, about 4 hours, about 6 hours or about 8 hours. In a most preferred embodiment, the concentration of lindane is about 0.5 percent (w/w) and the lotion is in contact with the skin for about 90 minutes. Generally, the lotion is topically applied once.

The method may further include administering, in association with the lindane lotion, at least one additional therapeutic agent in an amount sufficient to provide a therapeutic effect. The administering is typically concurrent with topically applying the lindane lotion. The at least additional therapeutic agent generally includes at least one of cetirizine, pheniramine maleate, or a combination thereof.

Advantageously, systemic drug exposure of the patient to the lindane lotion is reduced when compared to systemic drug exposure for a 1 percent (w/w) lindane lotion applied to the patient's skin for 8 hours. In one embodiment, exposure is reduced by at least about 5 percent. In a preferred embodiment, the exposure is reduced by at least about 20 percent.

The present invention further relates to a lotion that includes about 0.2 percent to less than 0.5 percent (w/w) lindane, or more than 0.5 percent to less than 0.95 percent (w/w) lindane, and a pharmaceutically acceptable carrier. Preferably, the lindane is present in an amount of about 0.25 percent to 0.49 percent (w/w) or 0.51 percent to 0.8 percent (w/w). More preferably, the lindane is present in an amount of about 0.25 percent (w/w) or about 0.75 percent (w/w).

The pharmaceutically acceptable carrier typically includes one or more of a surfactant component, thickening agent, emulsifying agent, emollient component, perfuming agent, colorant agent, preservative component, or buffering agent. Preferably, the surfactant component includes glyceryl monostearate; the thickening agent includes carrageenan; the emulsifying agent includes stearic acid, triethanolamine, 2-amino-2-methyl-1-propanol, or a combination thereof; the emollient component includes glyceryl monostearate, cetyl alcohol, or a combination thereof; the preservative agent includes methyl paraben, propyl paraben, or a combination thereof; and the buffering agent includes 2-amino-2-methyl-1-propanol. In one preferred embodiment, the carrier includes glycerol monostearate, carrageenan, stearic acid, triethanolamine, cetyl alcohol, at least one paraben, and 2-amino-2-methyl-1-propanol. In an exemplary embodiment, the glycerol monostearate is present in an amount of about 3% to 4% (w/w), the carrageenan is present in an amount of about 0.2% to 0.4% (w/w), the stearic acid is present in an amount of about 0.5% to 1.5% (w/w), the triethanolamine is present in an amount of about 0.25% to 0.75% (w/w), the cetyl alcohol is present in an amount of about 0.25% to 0.75% (w/w), the at least one paraben comprises methyl paraben and propyl paraben collectively present in an amount of about 0.05% to 0.3% (w/w), and the 2-amino-2-methyl-1-propanol is present in an amount of about 0.02% to 0.04% (w/w).

BRIEF DESCRIPTION OF THE DRAWINGS

Further features and advantages of the invention can be ascertained from the detailed description that is provided below in connection with the following drawing(s).

DETAILED DESCRIPTION OF THE PREFERRED EMBODIMENTS

Figure 1:
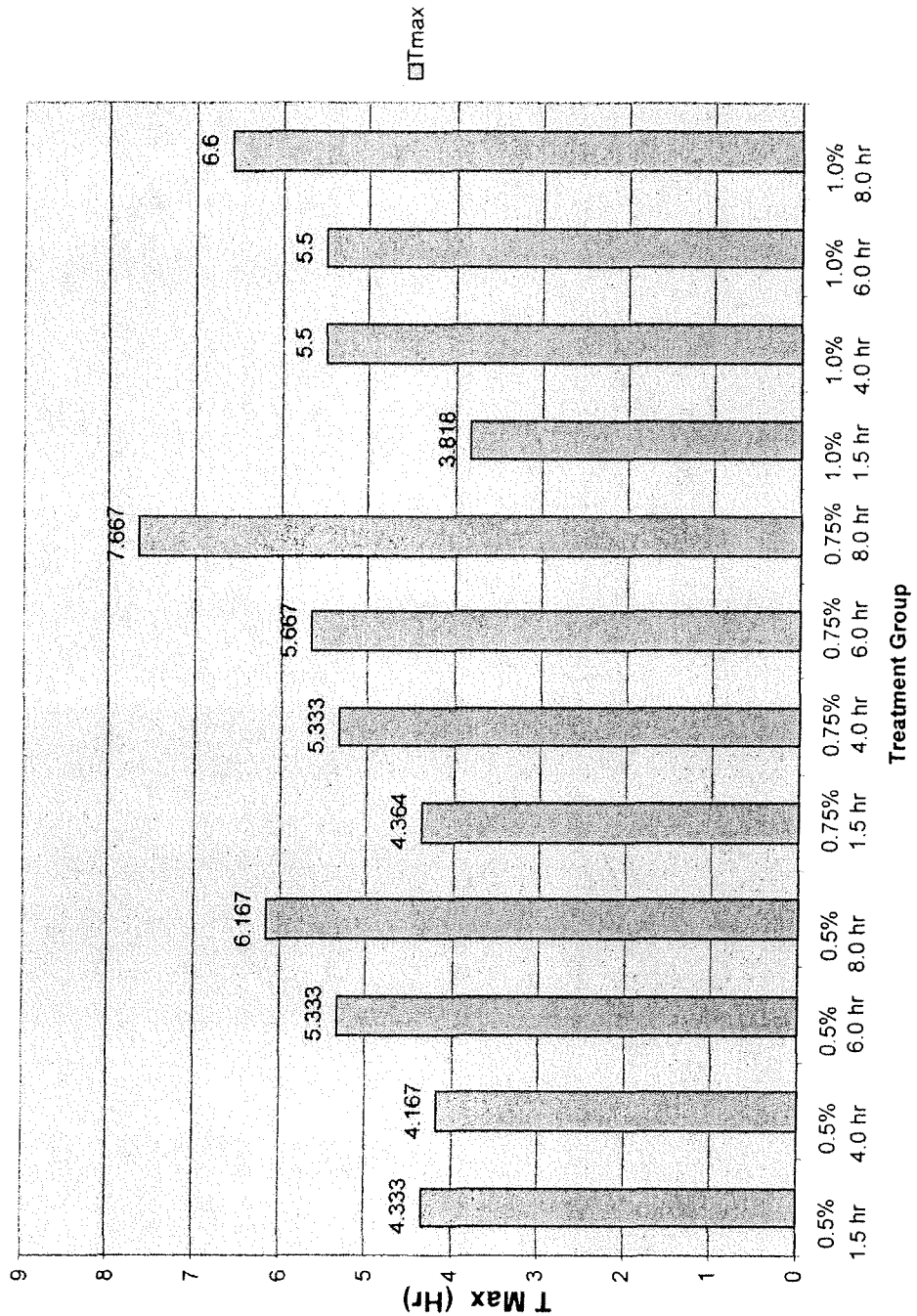
FIG. 1 is a graph showing the comparison of $T_{max}$ for different treatment regimens, both according to the prior art and according to the invention.

The present invention advantageously provides methods for the treatment of scabies that increases the margin of safety without comprising efficacy, i.e., the risk of serious adverse effects concomitant with administration of the FDA-approved 1% lindane lotion for 8 hours are minimized or avoided with the methods and compositions of the present invention without significant modification in therapeutic efficacy. Various methods of enhancing the risk-benefit balance of lindane lotion for the treatment of scabies infestation are included within the invention. In particular, a lower systemic drug exposure is achieved by reducing the concentration of lindane, shortening contact times relative to the current FDA-approved regimen of 1% lindane applied for 8 hours, or both. The invention encompasses administering a lindane lotion in an amount of less than 1% (w/w), administering the lotion for less than 8 hours, or both a lesser amount for a lesser time. For example, in one embodiment, when a 0.5% lotion is administered, it is not for 8 hours. The lesser amount, shorter application time, or both, are sufficient to decrease systemic lindane exposure in the patient, to minimize or avoid adverse effects, or both.

Any lotion available to those of ordinary skill in the art can be used to administer lindane for the desired time and/or in the desired amount. Typically, lotions are a low- to medium-viscosity medicated or non-medicated topical preparation intended for application to unbroken skin. Most lotions are oil-in-water emulsions and these are preferred because they are not soluble in sweat or other water-based materials, but water-in-oil lotions can also be formulated. Lotions are usually applied to external skin with a textile material, such as a clean cloth of cotton or wool, or gauze. It is not uncommon for the same active pharmaceutical ingredient to be formulated into one or more of a lotion, cream or ointment. Lotions are less viscous than creams and may be readily applied to regions of hairy skin such as the scalp. Lotions also have an advantage in that they may be spread thinly to better regulate administration of medications compared to a cream or ointment, and as a result lotions may more economically cover a large area of skin.

The inventive method may include topically applying to a patient's skin in need of treatment a 1 percent (w/w) lindane lotion, and leaving the lotion in contact with the skin for less than 6 hours, preferably from about 90 minutes to 4 hours. According to the invention, applying lindane lotions at this concentration, and for this time, is still similarly effective in treating scabies, when compared to the same concentration applied for a full 8 hours. The lotion is usually applied once topically to the patient's skin. Systemic drug exposure of the patient to the lindane is typically reduced in this treatment method when compared to a skin contact time of about 8 hours. Preferably, the systemic lindane exposure is reduced by at least about 30 percent.

The present invention relates to a method for the treatment of scabies that includes topically applying to a patient's skin in need of treatment a lotion with a concentration of less than 1 percent (w/w) lindane, and leaving the lotion in contact with skin for about 8 hours or less. In this case, not only is the concentration of lindane reduced, but in certain instances, the contact time with the skin is reduced as well.

The concentration of lindane is less than 1 percent (w/w), preferably about 0.1 percent to 0.95 percent (w/w) of the lotion, and more preferably about 0.2 percent to 0.8 percent (w/w) of the lotion. In another preferred embodiment, lindane is present in an amount of about 0.35 percent to 0.95 percent (w/w), and more preferably in an amount of about 0.4 percent to 0.75 percent (w/w). In various preferred embodiments, the lindane concentration is about 0.3 percent (w/w), about 0.5 percent (w/w), or about 0.75 percent (w/w). The lotion is generally in contact with the skin for about 90 minutes to less than about 8 hours, provided that less than 1 percent (w/w) is included when the administration time is 8 hours. Preferably, the administration time is about 90 minutes, about 2 hours, about 4 hours, about 6 hours, or about 8 hours. In a most preferred embodiment, the concentration of lindane is about 0.5 percent (w/w) and the lotion is in contact with the skin for about 90 minutes. The lotion is typically applied once for treatment.

Systemic drug exposure of the patient to the lindane lotion prepared and administered according to the invention is advantageously reduced when compared to systemic drug exposure for a 1 percent (w/w) lindane lotion applied to the patient's skin for 8 hours. In one embodiment, the exposure is reduced by at least about 5 percent, while in another, exposure is reduced by at least about 20 percent.

It may be necessary to vary the dosages within the parameters of the invention as described herein, as will be apparent to those of ordinary skill in the art. Further, it is noted that the clinician or treating physician will know how and when to interrupt, adjust, or terminate therapy in conjunction with individual patient response.

Advantageously, the methods of the present invention also include administering, in association with the lindane lotion, at least one additional therapeutic agent in an amount sufficient to provide a therapeutic effect. Any desired therapeutic agent can be included, preferably those that help treat the effects of scabies, or those that can be formulated as a topical treatment and more preferably as a lotion. Preferably, the administering is concurrent with topically applying the lindane lotion, for example, an antihistamine tablet and a lindane lotion. The term "in an amount sufficient to provide a therapeutic effect" includes an amount of an agent that is required to obtain prophylactic or therapeutic efficacy against a disease or condition, or a symptom thereof, or to manage a disease or condition, or a symptom thereof.

The additional therapeutic agent typically may include one or more medications that relieve itching, i.e., pruritus, but preferably includes at least one antihistamine or a combination thereof. A more preferred antihistamine includes pheniramine maleate and/or cetirizine, or a metabolite or salt thereof. Cetirizine is commercially available under the brand name Zyrtec®, and is supplied in tablet, chewable tablet, extended release tablet, or syrup form. Another suitable antihistamine includes loratadine, or a salt or metabolite thereof. Loratadine is commercially available as Claritin® and desloratadine is commercially available as Clarinex®, and these are typically supplied in tablet, orally disintegrating tablet, or syrup form as well. Pheniramine maleate is commercially available outside the United States under the brand name Avil®, and is supplied in tablet, syrup, and injectible form. Other topically adapted medicines that might enhance penetration or absorption of medicines through the skin should be minimized or avoided during treatment to help minimize or avoid the risk of increasing systemic lindane exposure and thereby increasing the risk of an adverse effect in a patient.

In addition, the present invention relates to a lotion that includes about 0.2 percent to less than 0.5 percent (w/w) lindane, or more than 0.5 percent to less than 0.9 percent (w/w) lindane, and a pharmaceutically acceptable carrier. Preferably, the lindane in the lotion is present in an amount of about 0.25 percent to 0.49 percent (w/w) or 0.51 percent to 0.8 percent (w/w), and more preferably, the lindane is present in an amount of about 0.25 percent (w/w) or about 0.75 percent (w/w). In other preferred embodiments, the lindane can be present in the lotion in an amount of about 0.35 percent to 0.75 percent (w/w), or in an amount of about 0.4 percent to 0.65 percent (w/w), in each case excluding 0.5 percent (w/w) in a one embodiment.

While any suitable pharmaceutically acceptable carrier can be used to formulate the lindane composition for topical treatment, preferably the carrier is adapted to provide a lotion. The pharmaceutically acceptable carrier typically includes one or more of a surfactant component, thickening agent, emulsifying agent, emollient component, perfuming agent, colorant agent, preservative component, buffering agent, anti-whitening or anti-foaming agent, antioxidant component, coloring agent, or chelating agent.

A surfactant component that can be included in the lotions of the present invention, when used, include one or more of stearic acid, cetyl alcohol, glyceryl monostearate, stearyl alcohol, sodium lauryl sulfate, fatty alcohols, ether sulfates, disodium-n-lauryl-(-imino dipropionate, polyoxyethylinized castor oil, sorbitan monooleate, sorbitan monostearate, lecithin, polyoxyethylene stearate, alkyl phenol polyglycol ether, cetyltrimethyl ammonium chloride, mono/dialkylpolyglycol ether orthophosphorus acid ester monoethanolamine salts, polyoxyalkene oxides of $C_{14}$-$C_{20}$ fatty alcohols, polyoxyalkylene sorbitan esters, propylene glycol monostearate, or the non-ionic polyoxyalkylene derivatives of hexitol anhydride partial long chain fatty acid esters, e.g., the polyoxyalkylene derivatives of sorbitan monolaurate, sorbitan monopalmitate, sorbitan monostearate, sorbitan tristearate, sorbitan monooleate or sorbitan trioleate, or mixtures thereof. Commercially available surfactants include Cetomacrogol® 1000 (Crodor Inc.), Ceteth-20®, Tween® 40, and Brig® 78. The surfactant component will typically form about 0.01 to 5 weight percent, preferably 0.25 to 3.5 weight percent, and more preferably about 0.5 to 2 weight percent of the total weight of the lotion. In a more preferred embodiment, the surfactant will provide about 0.75 to 3.5 weight percent of the lotion.

A thickening or viscosity-increasing agent aids in the attainment of the desired texture and spreadability. Preferably, the thickening agent includes carrageenan; carboxypolymethylene; one or more of a fatty acid alcohol, preferably a $C_{14}$-$C_{20}$ fatty acid alcohol or mixtures thereof, such as cetyl alcohol, stearyl alcohol, and cetostearyl alcohol; monoglycerides; or fatty acid esters of alcohols having from about 3 to about 16 carbon atoms; or a combination thereof. Examples of suitable monoglycerides are glyceryl monostearate and glyceryl monopalmitate. Examples of suitable esters are myristyl stearate and cetyl stearate. Commercially available thickening agents include Carbomer 940, an acrylic acid polymer having an approximate molecular weight of 4,000,000 and available from B. F. Goodrich Chemical Company; Klucel®, hydroxypropyl cellulose that is a propylene glycol ether of cellulose available from Hercules Inc.; Methocel® A, methyl cellulose which is a methyl ether of cellulose available from Dow Chemicals; and Polyquatemium-10, which is a polymeric quaternary ammonium salt of hydroxyethyl cellulose reacted with a trimethyl ammonium substituted epoxide, available from Amerchol Corp. The thickening agent will typically form about 0.1 to 5 weight percent, preferably about 0.2 to 4 weight percent, and more preferably about 0.3 to 2.5 weight percent, of the total weight of the lotion.

An emulsifying or solubilizing agent is generally used for dispersing insoluble drugs in an aqueous liquid finely and uniformly. The emulsifying agent, when included, should be non-toxic to human or other mammalian patients, and is preferably a pharmaceutically acceptable natural emulsifier or synthetic emulsifier. As the natural emulsifiers, various types of emulsifiers derived from animals or plants may be included in the emulsifying or solubilizing agent. For example, yolk lecithin, soybean lecithin or a hydrogenated substance thereof, phosphatidylcholine, phosphatidylserine, sphingomyelin, gum arabic, or gelatin, or a combination thereof, can be used in the optional emulsifying or solubilizing agent. As a synthetic emulsifier, one or more surface active agents of the cation, anion or nonionic type may be used. Typical examples of a suitable nonionic surface active agent include triethanolamine, stearic acid, 2-amino-2-methyl-1-propanol, and those of the castor oil type, and in particular, HCO (polyoxyethylene-hardened castor oil) type, or any combination thereof. In addition to the above examples, polyoxyethylene sorbitan fatty acid ester derivatives, such as polysorbate 80; glycerin fatty acid ester derivatives, such as glyceryl monocaprylate; polyethylene fatty acid ester derivatives, such as polyoxyethylene 40 monostearate; fatty acid mono(or di)glycerides having a medium size chain, for example, fatty acid mono(or di)glycerides having 6 to 12 carbon atoms, such as caprylic acid diglyceride, caprylic acid monoglyceride, or caproic acid diglyceride; or polyoxyethylated glycerides, such as polyoxyethylated oleic acid glyceride may be used in any combination. The emulsifying agent, when present, will typically form about 0.01 weight percent to about 4 weight percent, preferably about 0.5 weight percent to about 2.5 weight percent, and more preferably about 1 weight percent to about 2 weight percent, of the total weight of the lotion.

The emulsifying agents described above are typically used to provide the basic emulsifying function. If necessary or desired, an additional emulsifying agent may also be used. Examples of a suitable auxiliary or additional emulsifier agent include, for example, cholesterol, agar, magnesium hydroxide, methylcellulose, or pectin.

An emollient or skin conditioning agent can be included in the lotion of the present invention to provide a softening or soothing effect on the skin. The emollient agent typically also helps control the rate of evaporation and the tackiness of the lotion. A suitable emollient agent includes cholesterol, glycerine, cetostearyl alcohol, glycerol monostearate, petrolatum, glyceryl monooleate, myristyl alcohol, isopropyl palmitate, isopropyl myristate, lanolin alcohols, mineral oil, white soft paraffin, cetyl alcohol, or mixtures thereof. The emollient agent, when present, will typically form about 0.1 to 10 weight percent, preferably about 0.5 to 8 weight percent, and more preferably about 1 to 4.5 weight percent, of the total weight of the lotion.

Examples of a suitable preservative component that can be included in the lotions of the present invention include one or more of DMDM hydantoin, phenoxyethanol, parabens (e.g., methylparaben and propylparaben), chlorophenesin, benzyl alcohol, chlorhexidine gluconate, an ethyl alcohol and sodium methylparaben mixture (e.g., a pentylene glycol and sodium methylparaben mixture), methylchloroisothiazolinone, methylisothiazolinone, imidurea, propylene glycol, hydantoin derivatives, propionate salts, quaternium-15, imidazolidinyl urea, EDTA and its salts, 2-phenoxyethanol, or mixtures thereof. The preservative component, if present, will typically form about 0.01 to about 5 weight percent, preferably about 0.05 to about 3 weight percent, and more preferably about 0.1 to about 2 weight percent, of the total weight of the lotion.

A buffering agent preferably included in the lotion compositions can include a buffer solution of one or more of gluconate, lactate, oleate, citrate, acetate, phosphate, and/or carbonate salts, as well as triethanolamine or 2-amino-2-methyl-1-propanol, or any combination thereof. Such a buffering agent, if present, will typically form about 0.01 to 3 weight percent, preferably about 0.05 weight percent to about 1.5 weight percent, and more preferably about 0.1 weight percent to about 1 weight percent, of the total weight of the lotion.

An anti-foaming and anti-whitening agent may be included to increase the elegancy of the lotion and inhibit the formation of a white soapy look upon rubbing the lotion on the skin. Preferred examples include silicone fluid, dimethicone, or mixtures thereof. The anti-foaming agent, when included, will typically form about 0.2 to about 3 weight percent, preferably about 0.5 to about 1.5 weight percent, and more preferably about 0.75 to about 1 weight percent, of the total weight of the lotion.

An antioxidant component, if present, may include one or more compounds such as butylated hydroxytoluene, butylated hydroxyanisole, sodium metabisulfite, butylated hydroxytoluene, propyl gallate, sodium ascorbate, or mixtures thereof. The antioxidant component, if present, will typically form about 0.005 to about 0.1 weight percent, preferably from about 0.001 to about 0.075 weight percent, and more preferably from about 0.01 to about 0.03 weight percent, of the total weight of the lotion.

A perfuming agent, which is preferably non-irritating to the skin and soothing to the olfactory system in the vast majority of patients, may also be included. The perfuming agent may be any of the commercially available perfumes which are chemically-compatible with the components of the lotion, such as cocoa butter fragrance. Useful perfuming agents will include, for instance, floral oils such as rose oil, lilac, jasmine, wisteria, apple blossom, or compounds bouquets such as spice, aldehydic, woody, oriental, and the like, or any combination thereof. The perfuming agent, if present, will typically form about 0.01 to about 5 weight percent, preferably about 0.025 to about 2 weight percent, and more preferably about 0.05 to about 1.5 weight percent, of the total weight of the lotion.

One or more coloring agents may be included to provide an aesthetically pleasing color to the lotion. Colorant agents suitable for inclusion in the present invention include one or more water-soluble synthetic organic food additives (e.g., food dyes such as food red dye Nos. 2 and 3, food yellow dye Nos. 4 and 5 and food blue dye Nos. 1 and 2), water-insoluble lake dyes (e.g., aluminum salts of the above water-soluble synthetic organic food additives, etc.), and natural pigments (e.g., beta-carotene, chlorophyll, iron oxide red, etc.), and any combination thereof. Suitable coloring agents further include D&C Red No. 33, FD&C Red No. 3, FD&C Red No. 40, D&C Yellow No. 10, and C Yellow No. 6, and a mixture thereof. Such a colorant agent, if present, will typically form about 0.001 weight percent to about 1 weight percent, preferably about 0.005 weight percent to about 0.5 weight percent, and more preferably about 0.0075 weight percent to about 0.25 weight percent, of the total weight of the lotion.

Optionally, a chelating agent may be included as part of the carrier. A chelating agent can be added to trap metals that find their way into the compositions during processing, for example, to help reduce oxidation and increase stability of the formulation. Suitable chelating agents include, but are not limited to, one or more of dipotassium ethylenediamine tetraacetate dihydrate, ethylenediaminetetraacetic acid (EDTA), ethylenediamine (EDA), diethylenetriamine (DETA), aminoethylethanolamine (AEEA), and mixtures thereof. The chelating agent can be present in an amount of about 0.01 weight percent to about 3 weight percent, preferably about 0.05 weight percent to about 2 weight percent, and more preferably about 0.25 weight percent to about 1 weight percent, of the total weight of the lotion.

Examples of the liquid medium that can be used in the carrier of the present invention preferably include water, a lower alcohol, a glycol, glycerin, and mixtures thereof. Among them, water is preferred, and more preferably, distilled water because of its purity. As the lower alcohol, any lower alcohol may be used as far as it does not decompose the components in the lotion and does not irritate skin. For example, methanol, ethanol, or isopropyl alcohol, or one or more others may be used. As the glycol, preferably ethylene glycol, propylene glycol, butylene glycol and mono lower ethers thereof, can be used. The liquid medium will typically form about 50 to about 95 weight percent by weight, preferably 55 to about 90 weight percent, and more preferably from about 60 to about 85 weight percent, of the total weight of the lotion.

In a preferred embodiment, the lotion can include glyceryl monostearate, the carrageenan, stearic acid, triethanolamine, 2-amino-2-methyl-1-propanol, cetyl alcohol, and at least one paraben, e.g., methyl paraben, propyl paraben, or a combination thereof.

For this preferred lotion formulation, it should be understood that additional excipients or carriers may be included. Preferably, the glycerol monostearate is present in an amount of about 3% to 4% (w/w), the carrageenan is present in an amount of about 0.2% to 0.4% (w/w), the stearic acid is present in an amount of about 0.5% to 1.5% (w/w), the triethanolamine is present in an amount of about 0.25% to 0.75% (w/w), the cetyl alcohol is present in an amount of about 0.25% to 0.75% (w/w), the at least one paraben comprises methyl paraben and propyl paraben collectively present in an amount of about 0.05% to 0.3% (w/w), and the 2-amino-2-methyl-1-propanol is present in an amount of about 0.02% to 0.04% (w/w).

In a most preferred embodiment, the glycerol monostearate is present in an amount of about 3.5% (w/w), the carrageenan is present in an amount of about 0.3% (w/w), the stearic acid is present in an amount of about 1% (w/w), the triethanolamine is present in an amount of about 0.5% (w/w), the cetyl alcohol is present in an amount of about 0.5% (w/w), the methyl paraben and propyl paraben are each present in an amount of about 0.1% (w/w), and the 2-amino-2-methyl-1-propanol is present in an amount of about 0.03% (w/w).

As used herein, the term "scabies" refers to an infestation of the skin with the microscopic mite *Sarcoptes scabei*.

The term "about," as used herein, should generally be understood to refer to both numbers in a range of numerals. Moreover, all numerical ranges herein should be understood to include each hundredth of an integer.

Each of the patent applications, patents, publications, and other published documents mentioned or referred to in the Detailed Description is incorporated herein in its entirety by express reference thereto, to the same extent as if each individual patent application, patent, publication, and other published document was specifically and individually indicated to be incorporated by reference.

EXAMPLES

The invention is further defined by reference to the following examples, describing in detail the study used to investigate the compositions and methods of treatment of the present invention. These examples are for illustrative purposes only, and are not to be construed as limiting the appended claims.

Example 1

Study Design of Scabies Treatment

The study was conducted as a 4-week, multicenter, randomized, open-label, parallel-group trial to assess the safety, efficacy and pharmacokinetic behavior of varying topical lindane regimens for the management of scabies infestation. After a screening period, subjects meeting all inclusion study requirements were randomized to one of 12 topical lindane treatment groups—1% lindane lotion applied for 8 hours, 6 hours, 4 hours or 90 minutes; 0.75% lindane lotion applied for 8 hours, 6 hours, 4 hours or 90 minutes; or 0.5% lindane lotion applied for 8 hours, 6 hours, 4 hours or 90 minutes. The medication was applied as a one-time treatment.

Following treatment, subjects entered into a 4-week follow-up period to assess safety and efficacy of the lindane regimens tested. Standard measures for safety and efficacy were performed on Days 1, 7, 14 and 28. Blood samples for pharmacokinetic evaluation were taken on Day 1 at 0, 2, 4, 6, 8, and 24 hours after application of the lotion.

The goal of the study was to explore various methods of enhancing the risk-benefit balance of lindane lotion for the treatment of scabies infestation. Although 1% lindane lotion is considered safe and effective when used as currently labeled, systemic drug exposure has been raised as an issue, particularly for infants and small children and in situations of product misuse. As such, it was attempted to lower systemic drug exposure by reducing the concentration of lindane and/or shortening the application time. The FDA-approved 1% lindane lotion formulation applied for 8-12 hours served as the control.

Example 2

Treatment of Scabies in Patients

The study was initiated on May 25, 2005 and terminated on Oct. 25, 2005. During this time, 142 patients were enrolled and randomized to one of 12 lindane treatment regimens. The lotion was applied topically as a thin film over the patient's body from the neck down, and behind the ears by trained staff. The lotion was allowed to stay in contact with the skin for the specified time as a single application.

A total of 121 patients completed the study and 21 patients were prematurely discontinued. Fourteen patients were deemed not evaluable due to loss to follow up. In addition, two patients withdrew consent. In two cases, a fresh lesion of scabies was observed, while in another case, the patient's relative opposed participation. In one case, deviation from protocol ended the patient's participation. In one unusual case, the reason for withdrawal of the patient from the study was unknown. One patient was deemed not evaluable, despite completing the study, due to missing data for Days 7 and 14. As such, only 120 patients were considered evaluable for analysis of efficacy, and 22 patients were considered not evaluable.

TABLE 1

Treatment Details

| Lindane concentration | Contact time | No. of patients |
|---|---|---|
| 1.0% | 90 minutes | 12 |
|  | 4 hours | 12 |
|  | 6 hours | 12 |
|  | 8 hours | 11 |
| 0.75% | 90 minutes | 11 |
|  | 4 hours | 12 |
|  | 6 hours | 12 |
|  | 8 hours | 12 |
| 0.50% | 90 minutes | 12 |
|  | 4 hours | 12 |
|  | 6 hours | 12 |
|  | 8 hours | 12 |
| Total |  | 142 |

Example 3

Results of Lindane Treatment of Scabies

Overall efficacy results are provided in Table 2 below. Cure was defined as clearance of scabies infestation as determined clinically by the absence of fresh inflammation or new lesions and/or demonstration of the absence of scabies mites, eggs and/or scybala. All of the treatment arms proved to be equally effective in achieving clinical and microbiological cure. None of the investigational lindane lotion regimens were shown to be statistically significantly different from the efficacy of the FDA-controlled regimen of 1.0% administered for 8 hours.

TABLE 2

Overall Cure Rates Per Protocol*

| Lindane concentration | Contact time | No. of Patients | Responders | Non-Responders | Dropouts | Overall Cure Rate (%) |
|---|---|---|---|---|---|---|
| 1.0% | 90 minutes | 12 | 10 | 0 | 2 | |
| | 4 hours | 12 | 9 | 1 | 2 | |
| | 6 hours | 12 | 11 | 0 | 1 | |
| | 8 hours | 11 | 9 | 1 | 1 | |
| TOTAL | | 47 | 39 | 2 | 6 | 95% (39/41) |
| 0.75% | 90 minutes | 11 | 9 | 1 | 1 | |
| | 4 hours | 12 | 9 | 0 | 3 | |
| | 6 hours | 12 | 8 | 1 | 3 | |
| | 8 hours | 12 | 11 | 0 | 1 | |
| TOTAL | | 47 | 37 | 2 | 8 | 95% (37/39) |
| 0.50% | 90 minutes | 12 | 11 | 1 | 0 | |
| | 4 hours | 12 | 8 | 0 | 4 | |
| | 6 hours | 12 | 11 | 0 | 1 | |
| | 8 hours | 12 | 9 | 0 | 3 | |
| TOTAL | | 48 | 39 | 1 | 8 | 98% (39/40) |

*Only patients who fully complied with the study protocol through the final study visit were considered evaluable for per protocol analysis of efficacy.

As can be seen from the data, the majority of the patients responded positively to the different dosage regimens. Surprisingly, concentrations of lindane less than 1%, applied for contact times between 1.5 to 8 hours were effective in the treatment of scabies. Even 1% lindane applied for less than 8 hours was shown to be effective according to the invention.

Microbiologic assessment for the presence of mites, eggs or scybala was also performed for all patients at Screening, Day 7, Day 14, and Day 28 of the study. The results are summarized below in Table 3.

TABLE 3

Overall Microbiological Assessment

| Time | Positive findings | Negative findings | NA | Total |
|---|---|---|---|---|
| Screening | 41 | 101 | 0 | 142 |
| Day-7 | 3 | 118 | 21 | 142 |
| Day-14 | 0 | 107 | 35 | 142 |
| Day-28 | 0 | 102 | 40 | 142 |

Lindane lotion was found to be effective in the eradication of mites, eggs and scybala as assessed microscopically. At baseline, there were 41 patients with the presence of mites, eggs or scybala. At the first follow-up visit on Day 7, however, only 3 patients had microbiologic evidence of scabies. The three patients belonged to the following treatment groups: 1% lindane for 90 minutes, 0.5% lindane for 90 minutes, and 0.5% lindane for 8 hours. At the second and final follow-up visits on Days 14 and 28, none of the patients had positive microscopic findings for mites, eggs or scybala. Results of the microscopic examination results by treatment regimen are presented below in Table 4.

TABLE 4

Microbiological Assessment By Lindane Formulation

| | Lindane 1% | | | Lindane 0.75% | | | Lindane 0.50% | | |
|---|---|---|---|---|---|---|---|---|---|
| Time | Scabies (+) | Scabies (−) | NA | Scabies (+) | Scabies (−) | NA | Scabies (+) | Scabies (−) | NA |
| Screening | 16 (34%) | 31 | — | 11 (23%) | 36 | — | 14 (29%) | 34 | — |
| Day 7 | 1 | 39 | 7 | 0 | 42 | 5 | 2 | 37 | 9 |
| Day 14 | 0 | 35 | 12 | 0 | 38 | 9 | 0 | 34 | 14 |
| Day 28 | 0 | 34 | 13 | 0 | 35 | 12 | 0 | 33 | 15 |

All lindane regimens tested proved to be highly effective in achieving clinical and microbiological cure as assessed microscopically by the eradication of scabies mites, eggs and/or scybala. Moreover, 1% lindane lotion was equally effective in curing scabies infestation when applied for less than the currently recommended 8 hours (i.e., 6 hours, 4 hours and 90 minutes).

These findings demonstrate that lindane lotion can be applied in lower concentration, for shortened application times, or both, without compromising efficacy from that achieved with the currently approved 1% formulation applied for 8 hours. Similarly, lower concentrations of lindane than the approved 1% lotion formulation at 0.75% and 0.5% were surprisingly found to be equally effective in curing scabies, even when applied for shorter contact times than the currently recommended 8 hours (i.e., 6 hours, 4 hours and 90 minutes).

Scabies treatment failures, to date, are considered principally due to improper application, and/or failure to treat all contacts leading to reinfestation. However, there are reports of treatment tolerance and resistance to all commonly used scabicidal medications, including permethrin, crotamiton, ivermectin and lindane [Hernandez-Perez, E., et al., "*Resistance to antiscabietic drugs*", J. of the Am. Acad. of Derm., Vol. 8, pp. 1121-1122, 1983; Fraser, J., et al., "*Permethrin: a top end viewpoint and experience*", Med. J. of Australia, Vol. 160, p. 806, 1994; McCarthy J S, et al. 2004; Roberts, R. J., "*Clinical practice. Head lice*", N. Engl. J. Med., Vol. 346, No. 21, pp. 1645-1650, 2002; Johnston, G., et al. 2005; Currie, B. J., et al., "*First documentation of in vivo and in vitro ivermectin resistance in Sarcoptes scabiei*", Clin. Infect. Dis., Vol. 39, pp. e8-e12, 2004; Yoon, K. S., et al., "*Permethrin-resistant human head lice, Pediculus capitis, and their treatment*", Arch. Dermatol., Vol. 139, pp. 994-1000, 2003; Pollack, R. J, et al., "*Differential permethrin susceptibility of head lice sampled in the United States and Borneo*", Arch. Pediatr. Adolese. Med., Vol. 153, pp. 969-973, 1999; Downs, A. M., "*Managing head lice in an era of increasing resistance to insecticides*", Am. J. Clin. Dermatol., Vol. 5, No. 3, pp. 169-177, 2004]. Reports of resistance, however, particularly those relating to in vitro data, must be translated cautiously as they do not necessarily reflect cure rates that would be achieved clinically, nor are they easily extrapolated beyond the practice setting and geographical limits in which they were discovered [Yoon K S, et al. 2003]. The high rate of clinical cure noted in the present study supports such an effect. It also supports the current-day health benefits of lindane lotion for the management of scabies infestation.

Example 4

Pharmacokinetic Parameters of Lindane Treatment Study

Pharmacokinetic (PK) comparisons for the different lindane regimens studied are summarized below in Table 5. The extent of systemic drug exposure was assessed by $AUC_{0-t}$. There was a trend toward a reduction in exposure with shortened lindane lotion application times and lower lindane concentrations relative to the FDA-approved control regimen of 1.0% for 8 hours.

No significant differences were noted overall for $C_{max}$ by One-Way ANOVA. In contrast, the overall difference for $T_{max}$ was found to be statistically significant (p=0.0069) by Kruskal Wallis test as were between-group differences by Wilcoxon Rank Sum Test for the following lindane regimens compared with the control (i.e., 1.0% for 8 hours); 1.0% for 90 minutes; 0.75% for 90 minutes; 0.50% for 4 hours; and 0.05% for 90 minutes (p=0.0172, 0.0338, 0.0140 and 0.0153, respectively). Similarly, the overall difference for AUC was found to be statistically significant (p=0.0291). However, the small sample size per treatment group with a high Coefficient of Variance precluded a significant statistical test for between-group comparisons of AUC.

TABLE 5

Overall Pharmacokinetic Profiles By Treatment Groups

| Lindane concentration | Contact time | Number of Patients | Number of Patients with Lindane levels >100 ng/ml | Mean $T_{max}$ (hours) | Mean $C_{max}$ (ng/mL) | Mean $AUC_{0-t}$ (ng-hour/mL) | Change in AUC vs. Control (%) |
|---|---|---|---|---|---|---|---|
| 1.0% | 90 minutes | 12 | 3 | 3.818 | 57.525 | 604.27 | −34 |
|  | 4 hours | 12 | 0 | 5.5 | 41.334 | 478.345 | −48 |
|  | 6 hours | 12 | 3 | 5.5 | 69.131 | 993.336 | +9 |
|  | 8 hours | 11 | 2 | 6.6 | 62.417 | 911.497 | N/A* |
| TOTAL |  | 47 | 8 (17%) |  |  |  |  |
| 0.75% | 90 minutes | 11 | 1 | 4.364 | 61.391 | 493.477 | −46 |
|  | 4 hours | 12 | 2 | 5.333 | 68.625 | 695.768 | −24 |
|  | 6 hours | 12 | 1 | 5.667 | 57.994 | 749.141 | −18 |
|  | 8 hours | 12 | 2 | 7.667 | 62.388 | 869.355 | −5 |
| TOTAL |  | 47 | 6 (13%) |  |  |  |  |
| 0.50% | 90 minutes | 12 | 0 | 4.333 | 46.926 | 478.447 | −48 |
|  | 4 hours | 12 | 1 | 4.167 | 62.209 | 646.464 | −29 |
|  | 6 hours | 12 | 1 | 5.333 | 43.344 | 456.795 | −50 |
|  | 8 | 12 | 0 | 6.167 | 58.398 | 581.011 | −36 |
| TOTAL |  | 48 | 2 (4%) |  |  |  |  |

*Control = FDA-approved regimen.

As expected, the 0.5% lindane group had the lowest rate (4%) of subjects with lindane blood levels greater than 100 ng/mL compared with the 0.75% (13% of subjects) and 1% (17% of subjects) lindane groups. The difference reached statistical significance for the 0.5% lindane group versus the 1.0% lindane group (p=0.05). Additional logistic regression analyses were also performed for $C_{max}$ levels above and below 100 ng/mL. None of the independent factors within the logistic regression model, including age (adults vs. children), treatment regimen, or weight and height, were found to be statistically significant.

Figure 2:
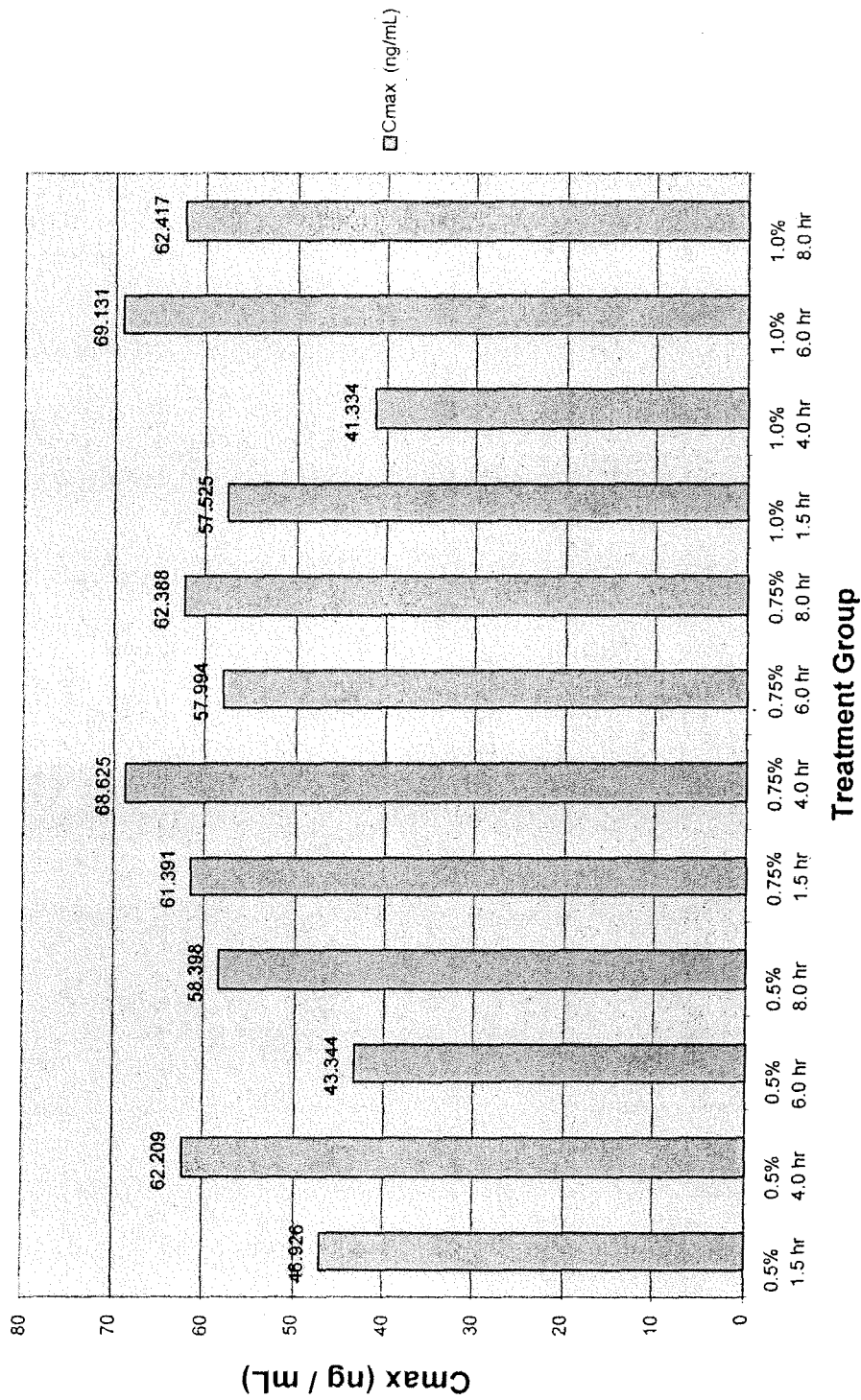
FIG. 2 is a graph showing the comparison of $C_{max}$ for different treatment regimens, both according to the prior art and according to the invention.
Figure 3:
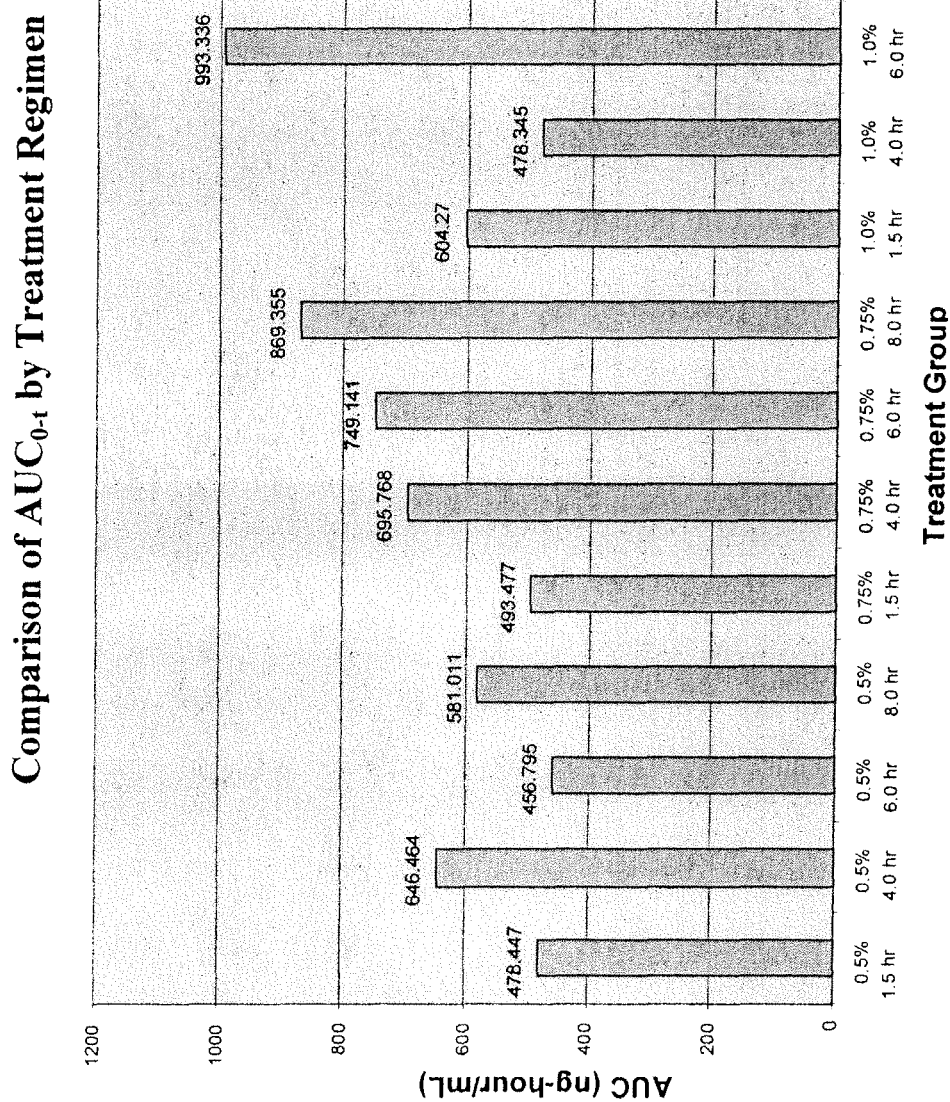
FIG. 3 is a graph showing the comparison of $AUC_{0-t}$ for different treatment regimens, both according to the prior art and according to the invention.

Pharmacokinetic parameters (i.e., $T_{max}$, $C_{max}$, and $AUC_{0-t}$) are also shown graphically in FIGS. 1-3. As can be readily seen, lower contact times of 1% lindane reduced systemic drug exposure by at least about 30%. For example, 1% lindane applied for 90 minutes resulted in a mean $AUC_{0-t}$, which measures the extent of systemic drug exposure, of 604.27 ng-hr/mL, compared to a value of 911.497 ng-hr/mL for 1% lindane applied for 8 hours. This is a difference of 307.227 ng-hr/mL. Dividing this difference by 911.497 ng-hr/mL yields a percentage of about 34%.

Similarly, 0.75% lindane applied for 8 hours reduced systemic drug exposure by about 5%, and 0.75% lindane applied for 4 hours reduced systemic drug exposure by about 20%, when compared to 1% lindane applied for 8 hours. In this study, systemic lindane drug exposure as measured by AUC was reduced by 48% when dosed at 0.5% lindane for 90 minutes versus the currently approved regimen of 1% for the full 8 hours. There was a trend toward lower systemic drug exposure, as measured by $AUC_{0-t}$, with shortened application times (i.e., 6, 4 and 1.5 hours) and lower concentrations of active pharmaceutical ingredient (i.e., 0.75% and 0.5% lindane). Again, small sample size per treatment arm and a high Coefficient of Variance precluded a significant statistical test for between-group AUC comparisons, although a significant difference was noted overall.

Although four subjects had a blood level of greater than 150 ng/mL of lindane (203.24, 154.77, 154.07, and 165.57), none of these patients had any abnormal neurologic findings or reported adverse events. Similarly, no adverse events, neurological or otherwise, were recorded for any of these patients. There was no apparent relationship between the dose of lindane and respective contact time with the likelihood of a high $C_{max}$, which occurred in the following lindane treatment regimens: 1% for 6 hours; 0.75% for 4 hours; 0.75% for 90 minutes; and 0.5% for 4 hours. None of the four patients were exceptionally young (age range: 13-24 years). In fact, children in this study did not demonstrate higher blood levels than adults, as has been previously suggested [U.S. FDA Public Health Advisory, 2003]. Additional multiple regression analyses showed that higher blood levels, with $C_{max}$>100 ng/mL, were not associated with age, gender, weight or age.

TABLE 6

Pharmacokinetic Profiles By Age

| Age group (years) | No. of Patients | Number of Patients with Lindane blood level >100 ng/ml | Mean $T_{max}$ (hours) | Mean $C_{max}$ (ng/mL) | Mean $AUC_{0-t}$ (ng-hour/mL) |
|---|---|---|---|---|---|
| 5 to 17 | 27 | 3 (11%) | 4.888 | 62.887 | 635.355 |
| 18 to 45 | 115 | 13 (11%) | 5.478 | 56.334 | 669.003 |

TABLE 7

Pharmacokinetic Profiles by Weight

| Weight | N | $T_{max}$ (hours) ± S.D | Mean $C_{max}$ (ng/mL) ± S.D | $AUC_{0-t}$ (ng-hour/mL) ± S.D |
|---|---|---|---|---|
| <50 Kgs | 54 | 5.434 ± 3.2905* | 67.819 ± 34.289 | 804.76 ± 398.01 |
| >50 Kgs | 88 | 5.333 ± 2.0154** | 51.297 ± 35.713 | 575.38 ± 473.27 |
| p-Value | | 0.8413 (N.S) | 0.0074 (S) | 0.0035 (S) |

N.S. = Not Significant; S = Significant
Note
*N = 53,
**N = 87 Since for one subject all concentrations were found to be Zero thus Tmax was undefined There was no apparent difference in the PK profiles noted for adults (≥18 years) and adolescents and children (≥18 years). However, patient weight below 50 kg (110 lbs) was associated with significantly higher maximum blood levels (i.e., $C_{max}$) and greater extent of exposure (i.e., AUC) compared with patients weighing 50 kg or more (Table 7). This finding is not unexpected and is consistent with the approved U.S. prescription label for lindane lotion, 1.0% USP. There was no apparent difference in pharmacokinetic profiles (i.e., $C_{max}$, $T_{max}$, and $AUC_{0-t}$) noted for adults compared with adolescents and children. Similarly, there was no difference in the proportion of older and younger subjects with higher lindane blood levels greater than 100 ng/mL.

TABLE 8

Pharmacokinetic Profiles by BSA

| BSA Strata | N | Mean $T_{max}$ (hours) ± S.D | Mean $C_{max}$ (ng/mL) ± S.D. | Mean $AUC_{0-t}$ (ng-hour/mL) ± S.D. |
|---|---|---|---|---|
| <1.65 m² | 122 | 5.327 ± 2.7043 | 58.539 ± 35.0495 | 668.561 ± 431.6703 |
| 1.66-2.04 m² | 18 | 5.333 ± 2.0580 | 51.103 ± 41.0240 | 635.9222 ± 617.3047 |
| p-Value | | 0.9935 | 0.4127 | 0.8309 |

BSA = Body Surface Area
NS = Overall difference not statistically significant, p > 0.05.

TABLE 9

Pharmacokinetic Profile by BMI (Adults Only)

| BMI Strata | N | Mean $T_{max}$ (hours) ± S.D. | Mean $C_{max}$ (ng/mL) ± S.D | Mean $AUC_{0-t}$ (ng-hour/mL) ± S.D |
|---|---|---|---|---|
| Underweight (<18.5) | 43 | 5.44 ± 3.55 | 68.85 ± 35.52 | 750.54 ± 398.70 |
| Normal (18.5-24.9) | 78 | 5.21 ± 1.85 | 54.02 ± 34.93 | 627.79 ± 435.81 |
| Overweight (25.0-29.9) | 17 | 6.24 ± 2.22 | 46.27 ± 34.31 | 628.96 ± 615.44 |
| Obese (≥30.0) | 4 | 4.00 ± 2.83 | 54.04 ± 51.45 | 539.23 ± 769.25 |
| p-Value | | 0.34 (NS) | 0.08 (NS) | 0.50 (NS) |

BMI = Body Mass Index
NS = Overall difference not statistically significant, p < 0.05.

No significant difference in lindane exposure was observed by patient BSA (Table 8). Similarly, there was no difference in exposure noted for adult patients classified as underweight, normal weight, overweight and obese by BMI strata (Table 9).

A difference in exposure was demonstrated by body weight. Patients under 50 kg (110 lbs) had significantly higher maximum blood levels (i.e., $C_{max}$) and greater extent of exposure (i.e., AUC) compared with patients weighing 50 kg or more (Table 42).

Example 5

Adverse Events

Adverse events (AEs) were monitored throughout the study by physical examination, including neurologic assessments, hematologic lab evaluations and patient diaries. Relatively few patients (14 out of 142) reported an AE during the study. Treatment-emergent events included itching, headache, dizziness and burning—all of which are consistent with the FDA-approved prescription labeling for 1% lindane lotion. All AEs were mild to moderate in severity, lasting anywhere from 7 to 21 days. No serious AEs, including serious neurologic AEs (e.g., seizure) or death, were reported for any of the patients during the course of the study. Table 5 below details the AEs that were reported during the study. Table 11 provides a brief summary of the AEs recorded.

TABLE 10

Initial Occurrence Of Adverse Events

| Time | Yes | No | NA |
|---|---|---|---|
| Screening | 0 | 142 | — |
| Day-1 (Treatment) | 1 | 141 | — |
| Day-7 | 8 | 124 | 10* |
| Day-14 | 6 | 116 | 20* |
| Day-28 | 6 | 114 | 22* |

NA = Not Applicable.
*Patients were prematurely discontinued.

Fourteen of the 142 patients enrolled in the study reported a total of 17 AEs. Some were prolonged in duration, lasting anywhere between 7 and 21 days; none were considered serious. Lindane lotion at a concentration of 0.5% was associated with the fewest number of reported AEs (3 vs. 6 and 8 for patients treated with 1% and 0.75% lindane, respectively). No new or unexpected AEs from those reported in the current FDA-approved 1% lindane lotion, USP prescription label were noted.

The $C_{max}$ values were recorded on Day 1 of the treatment. The AEs were recorded on Days 7, 14, and 21. The $C_{max}$ values for patients reporting AEs ranged from 6.08 ng/mL to 126.29 ng/ml. None of the patients with a reported AE had $C_{max}$ concentrations greater than 150 ng/mL. A direct correlation between peak systemic lindane levels and reported AEs was not demonstrated in this study.

TABLE 11

Summary Of Adverse Events Reported

| Lindane concentration | Reported AE | Relationship to Treatment | Duration of AE (Days) | $C_{max}$ (ng/mL) |
|---|---|---|---|---|
| 1.0% | Itching (new lesion at Day 21) | Possibly due to ineffectiveness | 21 | 6.08 |
| | Itching | Possible | 14 | 33.40 |
| | Itching | Possible | 7 | 29.16 |
| | Dizziness | Possible | 21 | 126.29 |
| | Headache | Possible | 14 | 102.74 |
| 0.75% | Headache followed by itching at Day 28 | Possible | 14 | 35.34 |
| | Headache | Possible | 7 | 103.69 |
| | Headache | Possible | 7 | 52.17 |
| | New lesion | Possibly due to ineffectiveness | 7 | 28.42 |
| | New lesion | Possibly due to ineffectiveness | 7 | 24.20 |
| | Dizziness | Possible | 7 | 31.78 |
| | Burning sensation | Possible | 7 | 58.18 |
| 0.50% | Itching & new lesion (scabies) | Possibly due to ineffectiveness | 7 | 65.09 |
| | Headache | Possible | 7 | 62.54 |

Example 6

Statistical Analysis of Lindane Treatment Study

The following are statistical comparisons for all of the investigational lindane regimens evaluated relative to the FDA-approved regimen, which served as the control. None of the regimens were shown to be statistically different from 1% lindane for 8 hours with respect to their efficacy. All of the treatment regimens proved to be equally effective in achieving clinical and microbiological cure. It is thus concluded that decreasing the concentration of lindane, shortening the contact time, or both, serve to enhance the margin of safety of topically applied lindane lotion without compromising its efficacy.

TABLE 12:

Statistical Treatment Comparisons (P Values)

| Lindane investigational regimen vs. lindane control (i.e., 1.0% for 8 hours) | | p Value | Statistical significance |
|---|---|---|---|
| 1.0% | 90 minutes | 1.0 | No |
| | 4 hours | 1.0 | No |
| | 6 hours | 0.4762 | No |
| 0.75% | 90 minutes | 1.0 | No |
| | 4 hours | 1.0 | No |
| | 6 hours | 1.0 | No |
| | 8 hours | 0.4762 | No |
| 0.50% | 90 minutes | 1.0 | No |
| | 4 hours | 1.0 | No |
| | 6 hours | 0.4762 | No |
| | 8 hours | 1.0 | No |

Example 6

Compositions of Lindane Lotion According to the Invention

The following exemplary lindane lotion compositions were prepared according to conventional methods known to those of skill in the art of preparing pharmaceutical lotions. All ingredients are listed in percentage by weight.

| Ingredient | 0.25% Lindane | 0.5% Lindane | 0.75% Lindane |
| --- | --- | --- | --- |
| Lindane, USP | 0.25 | 0.5 | 0.75 |
| Propylene Glycol, USP | 10.0 | 10.0 | 10.0 |
| Carrageenan, NF | 0.3 | 0.3 | 0.3 |
| Methyl Paraben | 0.1 | 0.1 | 0.1 |
| Propyl Paraben | 0.1 | 0.1 | 0.1 |
| Triethanolamine, NF | 0.5 | 0.5 | 0.5 |
| 2-Amino-2-Methyl-1-Propanol (AMP-95) | 0.03 | 0.03 | 0.03 |
| Glyceryl Monostearate, NF | 3.5 | 3.5 | 3.5 |
| Cetyl Alcohol, NF | 0.5 | 0.5 | 0.5 |
| Stearic Acid, NF | 1.0 | 1.0 | 1.0 |
| Cocoa Butter Fragrance F#1205 | 0.1 | 0.1 | 0.1 |
| Purified Water, USP | 83.62 | 83.37 | 83.12 |

Although preferred embodiments of the invention have been described in the foregoing description, it will be understood that the invention is not limited to the specific embodiments disclosed herein but is capable of numerous modifications by one of ordinary skill in the art. It will be understood that the materials used and the pharmaceutical details may be slightly different or modified from the descriptions herein without departing from the methods and compositions disclosed and taught by the present invention.

What is claimed is:

1. A method for the treatment of scabies, which comprises: topically applying to a patient's skin in need of the treatment a lotion with a concentration of 0.1 percent to 0.95 percent (w/w) lindane; and leaving the lotion in contact with skin for less than 6 hours, wherein systemic drug exposure of the patient to the lindane lotion is reduced when compared to systemic drug exposure for a 1 percent (w/w) lindane lotion is applied to the patient's skin for 8 hours.

2. The method of claim 1, wherein the concentration of lindane is 0.2 percent to 0.8 percent (w/w) of the lotion.

3. The method of claim 1, wherein the lotion is in contact with the skin for 90 minutes to less than 6 hours.

4. The method of claim 1, wherein the concentration of lindane is 0.5 percent (w/w) and the lotion is in contact with the skin for 90 minutes to 4 hours.

5. The method of claim 1, wherein the lotion is topically applied once.

6. The method of claim 1, further comprising administering, in association with the lindane lotion, at least one additional therapeutic agent in an amount sufficient to provide a therapeutic effect.

7. The method of claim 6, wherein the administering is concurrent with topically applying the lindane lotion.

8. The method of claim 6, wherein the additional therapeutic agent is selected from the group consisting of cetirizine, pheniramine maleate, or a combination thereof.

9. The method of claim 1, wherein the systemic drug exposure of the patient to the lindane solution is reduced by at least 5 percent to 20 percent.

10. A scabies treatment lotion for topical application for the treatment of scabies, comprising: 0.1 percent to 0.95 percent (w/w) lindane; and a pharmaceutically acceptable carrier comprising glycerol monostearate, carrageenan, stearic acid, triethanolamine, cetyl alcohol, at least one paraben, and 2-amino-2-methyl-1-propanol, wherein the glycerol monostearate is present in an amount of about 3 percent to 4 percent (w/w), the carrageenan is present in an amount of about 0.2 percent to 0.4 percent (w/w), the stearic acid is present in an amount of about 0.5 percent to 1.5 percent (w/w), the triethanolamine is present in an amount of about 0.25 percent to 0.75 percent (w/w), the cetyl alcohol is present in an amount of about 0.25 percent to 0.75 percent (w/w), the paraben is present in an amount of about 0.05 percent to 0.3 percent (w/w), and the 2-amino-2-methyl-1-propanol is present in an amount of about 0.02 percent to 0.04 percent (w/w).

11. A method for the treatment of scabies, which comprises topically applying to a patient's skin in need of the treatment the scabies treatment lotion of claim 10.

12. The method of claim 11 wherein the scabies treatment lotion has a concentration of 0.1 percent to 0.95 percent (w/w) lindane; and the method includes leaving the lotion in contact with skin for less than 6 hours, wherein systemic drug exposure of the patient to the lindane lotion is reduced when compared to systemic drug exposure for a 1 percent (w/w) lindane lotion is applied to the patient's skin for 8 hours.

* * * * *